United States Patent [19]

Padfield et al.

[11] Patent Number: 4,594,359

[45] Date of Patent: Jun. 10, 1986

[54] PHARMACEUTICAL COMPOSITIONS

[75] Inventors: John M. Padfield, Meldreth; Cheryl V. Groom, Barnard Castle, both of United Kingdom

[73] Assignee: Glaxo Group Limited, London, England

[21] Appl. No.: 593,432

[22] Filed: Mar. 26, 1984

Related U.S. Application Data

[63] Continuation of Ser. No. 498,724, May 27, 1983, abandoned.

[30] Foreign Application Priority Data

May 27, 1982 [GB] United Kingdom ............... 8215502

[51] Int. Cl.⁴ ............................................ A61K 31/135
[52] U.S. Cl. .................................................. 514/647
[58] Field of Search ...................... 424/330; 514/647

[56] References Cited

U.S. PATENT DOCUMENTS 3,705,233 12/1972 Lunts .................................. 424/45

OTHER PUBLICATIONS

Mercks Index, 9th Ed. (1976) p. 789.
L. B. Hakes et al., The Effect of Sugars on the Stability of Salbutamol Sulphate Solutions, J. Pharm. Pharmacology, line 32, 1980, p. 49P.

*Primary Examiner*—Stanley J. Friedman
*Attorney, Agent, or Firm*—Bacon & Thomas

[57] ABSTRACT

A pharmaceutical composition is described which contains as active ingredient the β-stimulant salbutamol or one or more of its physiologically acceptable salts. The stability of aqueous formulations of the composition is improved by including a cellulose derivative which provide an optically transparent or opalescent colloidal dispersion. Preferred compositions are liquid formulations suitable for oral administration in which the cellulose derivative also serves as a thickening agent.

14 Claims, No Drawings

PHARMACEUTICAL COMPOSITIONS

This application is a continuation of application Ser. No. 498,724, filed May 27, 1983, now abandoned.

The present invention relates to a pharmaceutical composition containing as active ingredient the β-stimulant salbutamol.

Salbutamol [($\alpha^1$-tert-butylaminomethyl)-4-hydroxy-m-xylene-$\alpha^1,\alpha^3$-diol)] and its physiologically acceptable salts are described in British Patent Specification No. 1200886. In that specification there is reference to pharmaceutical compositions containing salbutamol and there is a description of solid and liquid preparations for oral and intravenous use.

Liquid preparations of salbutamol and/or a physiologically acceptable salt thereof are conveniently water based and for oral use the preparations contain sucrose or sorbitol which acts both as a sweetener and thickening agent.

Such pharmaceutical compositions have been successfully marketed. However, it is known that the presence of a substance such as sucrose, or sorbitol or glycerol in aqueous compositions of salbutamol or a physiologically acceptable salt thereof is associated with an accelerated deterioration in the stability of the salbutamol in the composition.

We have now surprisingly found that the stability of salbutamol in aqueous formulations may be significantly enhanced by the presence of a cellulose derivative which forms a colloidal dispersion in water.

Thus, the present invention provides an improved pharmaceutical composition which comprises an aqueous dispersion of one or more cellulose derivatives containing salbutamol and/or one or more of its physiologically acceptable salts.

According to a preferred embodiment of the invention, the pharmaceutical composition is formulated as a liquid preparation suitable for oral administration in which the cellulose derivative is advantageously used as thickening agent.

Suitable cellulose derivatives are those which form an optically transparent or opalescent dispersion in water, preferably an optically transparent colloidal dispersion.

Preferred cellulose derivatives include non-ionic derivatives such as alkyl and/or hydroxyalkyl ethers of cellulose, particularly $C_{1-4}$ alkyl and/or hydroxy $C_{1-4}$ alkylethers of cellulose for example, ethyl cellulose, methyl cellulose, ethylmethyl cellulose, hydroxymethyl cellulose, hydroxyethyl cellulose, hydroxypropyl cellulose, hydroxyethyl methylcellulose, hydroxypropyl methylcellulose and hydroxyethyl ethylcellulose.

Suitable ionic cellulose derivatives include carboxymethylceullose and salts thereof such as the calcium or sodium salts.

Particularly preferred cellulose derivatives are hydroxyethyl cellulose and more especially hydroxypropyl methylcellulose.

A preferred salt of salbutamol for use in the pharmaceutical composition according to the invention is the sulphate.

The total amount of dispersible cellulose derivatives present in the pharmaceutical composition according to the invention is such that the resulting colloidal dispersion has the desired enhanced stability and has a viscosity suitable for its proposed mode of administration.

Preferably, the pharmaceutical composition contains at least 0.1% w/v of the cellulose derivatives.

For liquid preparations suitable for oral administration the total amount of cellulose derivatives will be determined primarily by the requirement to obtain a solution with a viscosity suitable for oral administration, preferably within the range 5 to 10,000 centipoises, more preferably from 10 to 100 centipoises.

The concentration of the salbutamol or its salts in the formulation may be adjusted to suit the use for which the formulation is required and/or the patient's requirements. For example, for oral use the concentration is conveniently equivalent to 1 mg to 4 mg, preferably, 2 mg, of salbutamol, expressed as salbutamol free base, per 5 ml of the liquid.

Preferably the pH of the pharmaceutical composition is in the range of from 2.5 to 7, more particularly 3.5 and this is conveniently achieved by the use of a buffer. For oral compositions, suitable buffers include a sodium citrate/citric acid buffer.

The pharmaceutical composition according to the invention may also contain an antimicrobial preservative, such as benzoic acid or a salt thereof which generates the acid in situ, or a methyl, ethyl, propyl or butyl hydroxybenzoate. For oral use the composition preferably also contains a flavouring, a sweetening agent such as saccharin sodium or sodium cyclamate and/or a colouring.

The pharmaceutical composition according to the invention may be prepared by dispersing one or more cellulose derivatives in water, and then adding or mixing with the salbutamol or physiologically acceptable salts thereof, conveniently dissolved in water, together with any optional components of the composition.

Illustrative examples of formulations (expressed as a 5 ml dose for oral administration according to the invention are as follows:

EXAMPLE 1

| | |
|---|---|
| Salbutamol sulphate | 2.40 mg |
| Hydroxyethyl cellulose (Natrosol 250 H) | 22.5 mg |
| Distilled water to | 5 ml |

To prepare the formulation the hydroxyethyl cellulose is dispersed in water and then mixed with a solution of salbutamol sulphate in water.

EXAMPLE 2

| | |
|---|---|
| Salbutamol sulphate | 2.40 mg |
| Sodium citrate dihydrate | 9.60 mg |
| Citric acid monohydrate | 15.15 mg |
| Natrosol 250 H | 15.0 mg |
| Distilled water to | 5.0 ml |

To prepare the formulation the hydroxyethyl cellulose is dispersed in water, and then mixed with a solution of salbutamol and the buffers salts in water.

EXAMPLE 3

| | |
|---|---|
| Salbutamol sulphate | 2.40 mg |
| Sodium citrate dihydrate | 9.60 mg |
| Citric acid monohydrate | 15.25 mg |
| Hydroxypropyl methylcellulose viscosity type 4000 | 22.5 mg |

| -continued | |
|---|---|
| Distilled water to | 5 ml |

EXAMPLE 4

| Salbutamol sulphate B.P. | 2.40 mg |
|---|---|
| Sodium citrate B.P. | 7.5 mg |
| Citric acid monohydrate B.P. | 25.0 mg |
| Hydroxypropyl methylcellulose (viscosity type 4000) | 22.5 mg |
| Sodium benzoate B.P. | 10.0 mg |
| Saccharin sodium B.P. | 2.5 mg |
| Flavouring | qS |
| Purified water to | 5 ml |

To prepare the formulations of Examples 3 and 4 the hydroxypropyl methylcellulose is dispersed in hot water, cooled and then mixed with an aqueous solution containing the salbutamol sulphate and the other components of the formulation.

We claim:

1. A pharmaceutical composition comprising an aqueous dispersion of one or more cellulose derivatives containing salbutamol and/or one or more of its physiologically acceptable salts, wherein the cellulose derivative is an alkyl and/or hydroxyalkyl ether of cellulose; carboxymethyl cellulose or salts thereof; and wherein the amount of cellulose derivative present in the composition is a salbutamol stabilizing effective amount of said cellulose derivative.

2. A pharmaceutical composition according to claim 1, which comprises the one or more cellulose derivatives in a total amount of at least 0.1% w/v.

3. A pharmaceutical composition according to claim 1, wherein the cellulose derivative is an alkyl and/or hydroxyalkyl ether.

4. A pharmaceutical composition according to claim 1, in which the cellulose derivative is selected from the group consisting of ethyl cellulose, methyl cellulose, ethylmethyl cellulose, hydroxymethyl cellulose, hydroxyethyl cellulose, hydroxypropyl cellulose, hydroxyethyl methylcellulose, hydroxypropyl methylcellulose, hydroxyethyl ethylcellulose, carboxymethylcellulose and salts of carboxymethylcellulose.

5. A pharmaceutical composition according to claim 4, wherein the cellulose derivative is hydroxypropyl methylcellulose.

6. A pharmaceutical composition according to claim 1, which is formulated as a liquid preparation suitable for oral administration.

7. A pharmaceutical composition according to claim 6, which contains the one or more cellulose derivatives in a total amount such as to provide the liquid preparation with a viscosity in the range of from 5 to 10,000 centipoises.

8. A pharmaceutical composition according to claim 7, wherein the viscosity is in the range of from 10 to 100 centipoises.

9. A pharmaceutical composition according to claim 6, which contains salbutamol and/or one or more of its physiologically acceptable salts in a concentration of 1 mg to 4 mg, expressed as salbutamol free base per 5 ml of liquid.

10. A pharmaceutical composition according to claim 9, wherein the concentration is 2 mg expressed as salbutamol free base per 5 ml of liquid.

11. A pharmaceutical composition according to claim 1, having a pH of 3.5.

12. A pharmaceutical composition according to claim 1 wherein the cellulose derivative is hydroxyethyl cellulose.

13. A pharmaceutical composition according to claim 1 which has a pH within the range of from 2.5 to 7.

14. A pharmaceutical composition according to claim 3 wherein the alkyl group and the alkyl moiety contain from 1 to 4 carbon atoms.

* * * * *

REEXAMINATION CERTIFICATE (2344th)
United States Patent [19]
Padfield et al.

[11] B1 4,594,359
[45] Certificate Issued Jul. 26, 1994

[54] PHARMACEUTICAL COMPOSITIONS

[75] Inventors: John M. Padfield, Meldreth; Cheryl V. Groom, Barnard Castle, both of United Kingdom

[73] Assignee: Glaxo Group Ltd., London, England

Reexamination Request:
No. 90/003,080, May 28, 1993

Reexamination Certificate for:
Patent No.: 4,594,359
Issued: Jun. 10, 1986
Appl. No.: 593,432
Filed: Mar. 26, 1984

Related U.S. Application Data

[63] Continuation of Ser. No. 498,724, May 27, 1983, abandoned.

[30] Foreign Application Priority Data

May 27, 1982 [GB] United Kingdom ............ 8215502

[51] Int. Cl.$^5$ .................................. A61K 31/135
[52] U.S. Cl. ........................................... 514/647
[58] Field of Search ............................. 514/647

[56] References Cited

U.S. PATENT DOCUMENTS

| | | | |
|---|---|---|---|
| 1,453,034 | 10/1976 | Zaimis . | |
| 3,818,101 | 6/1974 | Baile et al. | 514/646 |
| 4,499,108 | 2/1985 | Sequeira et al. | 514/653 |

FOREIGN PATENT DOCUMENTS

| | | |
|---|---|---|
| 171718 | 8/1973 | New Zealand . |
| 1200886 | 8/1970 | United Kingdom . |
| 1453034 | 10/1976 | United Kingdom . |

OTHER PUBLICATIONS

Remington's Pharmaceutical Sciences, 16th edition, 1980 p. 1245.

*Primary Examiner*—Raymond J. Henley, III

[57] ABSTRACT

A pharmaceutical composition is described which contains as active ingredient the $\beta$-stimulant salbutamol or one or more of its physiologically acceptable salts. The stability of aqueous formulations of the composition is improved by including a cellulose derivative which provide an optically transparent or opalescent colloidal dispersion. Preferred compositions are liquid formulations suitable for oral administration in which the cellulose derivative also serves as a thickening agent.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 3 is cancelled.

Claims 1 and 14 are determined to be patentable as amended.

Claims 2 and 4–13, dependent on an amended claim, are determined to be patentable.

1. A pharmaceutical composition comprising an aqueous dispersion of one or more cellulose derivatives containing salbutamol and/or one or more of its physiologically acceptable salts, wherein the cellulose derivative is an alkyl and/or hydroxyalkyl ether of cellulose; [carboxymethyl cellulose or salts thereof;] and wherein the amount of cellulose derivative present in the composition is a salbutamol stabilizing effective amount of said cellulose derivative.

14. A pharmaceutical composition according to claim [3] *1* wherein the alkyl group and the alkyl moiety contain from 1 to 4 carbon atoms.

* * * * *